United States Patent [19]

Drach et al.

[11] Patent Number: 4,720,383

[45] Date of Patent: Jan. 19, 1988

[54] SOFTENING AND CONDITIONING FIBERS WITH IMIDAZOLINIUM COMPOUNDS

[75] Inventors: John E. Drach, Cheltenham; Robert D. Evans, Warminster, both of Pa.; Joseph J. Fanelli, Alpharetta; Anthony J. O'Lenick, Jr., Lilburn, both of Ga.

[73] Assignee: Quaker Chemical Corporation, Pa.

[21] Appl. No.: 864,085

[22] Filed: May 16, 1986

[51] Int. Cl.$^4$ .................. A61K 7/075; C07D 233/18
[52] U.S. Cl. .......................... 424/70; 162/9; 162/72; 162/74; 252/8.6; 252/8.8; 548/349; 548/354
[58] Field of Search ............... 548/354, 349; 424/70; 252/8.6, 8.8; 162/9, 72, 74

[56] References Cited

U.S. PATENT DOCUMENTS 4,371,517  2/1983  Vanlerberghe et al. ............... 424/70

OTHER PUBLICATIONS

*Chemical Abstracts*, 82: 18569v (1975), [Ger. Offen. 2,360,723, 6/20/74, Loss et al.].

*Primary Examiner*—Richard A. Schwartz
*Attorney, Agent, or Firm*—Ladas & Parry

[57] ABSTRACT

Novel imidazolinium compounds, and a method of using the compounds for softening and conditioning fibers, hair and skin and as surfactants, and debonders for cellulose pulp having the general formula:

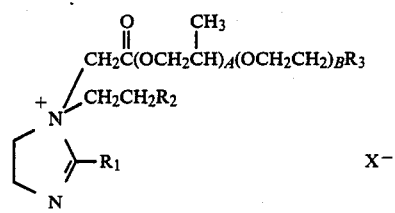

wherein $R_1$ is an n-alkyl, branched alkyl, alkenyl, branched alkenyl alkadienyl or branched alkadienyl group containing 8 to 21 carbon atoms; $R_2$ is a radical selected from the group consisting of (a) —OH, (b) amide radicals each of which has the structure

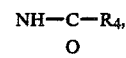

(c) a substituted imidazolinium group which has the structure:

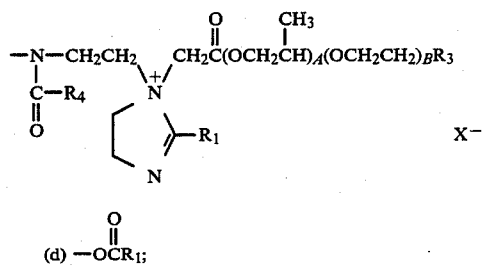

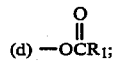

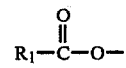

$R_3$ is a radical which has the structure $$R_1-\overset{\overset{O}{\|}}{C}-O-$$

or —$OR_5$; $R_4$ is an alkyl or alkenyl group containing 1 to 17 carbon atoms; $R_5$ is $R_1$ or mono or dialkyl phenyl; A is an integer of from 0 to 20 and B is an integer of from 0 to 20 and A+B>0; x is either chlorine or bromine are provided.

8 Claims, No Drawings

SOFTENING AND CONDITIONING FIBERS WITH IMIDAZOLINIUM COMPOUNDS

FIELD OF THE INVENTION

The object of this invention is to provide novel imidazolinium compounds, useful for softening and conditioning fibers, hair and skin, and as surfactants, and debonders for cellulose pulp having the general formula:

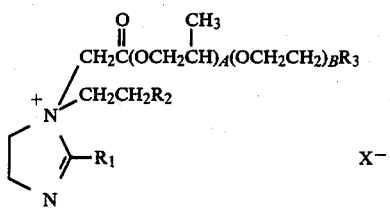

Formula I wherein $R_1$ is an n-alkyl, branched alkyl, alkenyl, branched alkenyl alkadienyl or branched alkadienyl group containing 8 to 21 carbon atoms; $R_2$ is a radical selected from the group consisting of (a) —OH, (b) amide radicals each of which has the structure

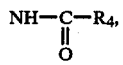

(c) a substituted imidazolinium group which has the structure:

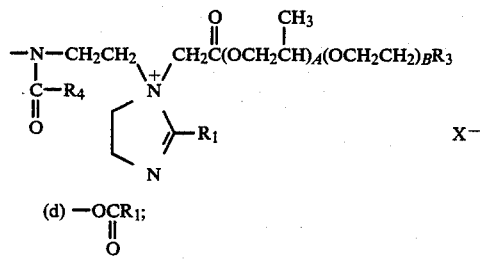

(d) —OCR$_1$;
$\quad\quad\;\;\|$
$\quad\quad\;\;O$ $R_3$ is a radical which has the structure

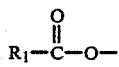

or —OR$_5$; $R_4$ is an alkyl or alkenyl group containing 1 to 17 carbon atoms; $R_5$ is $R_1$ or mono or dialkyl phenyl; A is an integer of from 0 to 20 and B is an integer of from 0 to 20 and A+B>0; x is either chlorine or bromine are provided.

It is another object of the invention to provide a method of softening and conditioning hair and textile fibers that is highly desirable, without the disadvantage of previously known quaternary compounds. These include to varying degrees, a marked ability to yellow the fabric, a tendency to build up upon repeated treatment, poor hand (i.e. softness and feel) and severe eye and skin irritation.

PRIOR ART

Quaternized alkoxylated fatty alkanoate esters have been described by Wechster et al in U.S. Pat. No. 4 370,272 having the general formula:

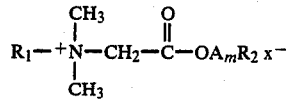

wherein $R_1$ is a radical selected from (a) a straight chain aliphatic radical containing from 12 to 24 carbon atoms, (b) ether radicals each of which has the structure: $R_3O(CH_2)_y$—wherein $R_3$ is a straight chain aliphatic radical containing from 8 to 18 carbon atoms and where y is an integer which is either 2 or 3, (c) amide radicals each of which has the structure

wherein $R_4$ is a straight chain aliphatic hydrocarbon radical containing from 7 to 17 carbon atoms and where y is an integer which is either 2 or 3, (d) ester radicals each of which has the structure

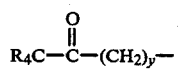

wherein $R_4$ is a straight chain aliphatic hydrocarbon radical containing from 7 to 17 carbon atoms and where y is an integer which is either 2 or 3; A is an alkoxy radical containing one oxygen atom and either two or three carbon atoms; $R_2$ is a straight chain aliphatic hydrocarbon radical containing from 12 to 32 carbon atoms; x is an atom selected from the group consisting of bromine and chlorine. These compounds were found to be useful as fabric softeners and hair conditions.

Conners and Fogel in U.S. Pat. No. 4,038,294 disclose fatty halo alkanoate quaternaries of dialkylaminopropylamides having the general formula:

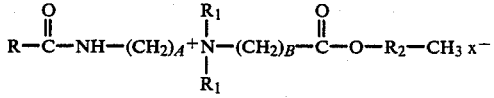

wherein the

moiety is selected from the group consisting of glyconic acid, and $C_7$-$C_{21}$ fatty acids; $R_1$ is an alkyl group having from 1 to 2 carbon atoms; $R_2$ is selected from the group consisting of $(CH_2)_{(7-21)}$ and sorbate; A is an integer of from 2 to 3; B is an integer of from 1 to 3; x is a halogen. These compounds were found to be excellent emollients having surprisingly good anti-tangle and antistatic properties in hair preparations.

Neither the compounds disclosed in U.S. Pat. Nos. 4,038,294 nor in 4,370,272 are derivatives of imidazolines, nor are they described as being useful as debonders for cellulose pulp fibers.

The properties of these novel quaternary compounds making them well suited for softening and conditioning fibers for applications (including debonding pulp) such as personal care, laundry and textile use is the fact that they are substantive to fibers, hair and skin and also very mild to the skin and eyes.

The standard prior art fabric softeners are quaternary compounds which are prepared by alkylating a tertiary amine with such agents as benzyl chloride or dimethyl sulfate or diethyl sulfate or methyl chloride. These materials are relatively inexpensive but offer several key disadvantages. These include variations in the ability to yellow the fabric, a tendency to build up upon repeated treatment, variability in hand (i.e. softness and feel) and severe eye and skin irritation. Few if any molecules have all the desireable properties. The added problem of incomplete reaction using the above mentioned alkylating agents leads to unreacted amine and a variety of semireacted alkylating agent products and potentially unreacted alkylating agent. These alkylating agents have been shown to be toxic. The standard softeners used are selected from the following classes:

Class #1:
Alkyl imidazoline quaternaries made from the alkylation of an imidazoline made by reacting diethylenetriamine, and a high molecular weight acid like stearic. The standard alkylating agents are diethyl sulfate or methyl chloride or dimethyl sulfate or methyl chloride or benzyl chloride.

Class #2:
tertiary amines quaternized with benzyl chloride or diethyl sulfate or methyl chloride or dimethyl sulfate.

Class #3:
Quaternaries of ethoxylated or nonethoxylated amido amines derived from the reaction of high molecular weight acid like stearic and a multi amine like diethylenetriamine. The standard alkylating agents are diethyl sulfate or dimethyl sulfate or methyl chloride or benzyl chloride.

Class #4:
Amido amine salts derived from partially acid neutralized amines.

As mentioned the standard cationic fabric softeners have a marked tendency to impart yellowness to fabrics, especially when the cationic is applied repeatedly. Further, most commercially available cationics have no compatability with anionics, forming insoluble complexes. U.S. Pat. No. 3,904,359 assigned to Colgate Palmolive describes a method of minimizing yellowness in fabrics by treating the fabric softening quaternary with a complexing acid, including citric, fumaric, adipic, succinic and mixtures thereof. The addition of these acids forms salts with residual amine compounds present as unreacted raw materials in the preparation of the quaternary. Additionally, U.S. Pat. Nos. 4,073,735 and 4,045,358 both assigned to Colgate Palmolive, teaches that addition of alkali metal silicates or terphthalic acid is also effective in minimizing yellowness. The same phenomenon is believed to occur, namely the formation of salts with residual amine compounds present as unreacted raw materials in the preparation of the amine. Addition of higher alcohol sulfates is also presented in U.S. Pat. No. 4,000,077. The addition of antioxidants like 4,4'-butylidenebis-(6-tert-butyl-3-methylphenol) is disclosed in U.S. Pat. No. 3,979,306. Another approach to nonyellowing softeners is to use expensive amphoterics. This is disclosed in U.S. Pat. No. 4,089,786. Minegishi describes in U.S. Pat. No. 4,144,177 the use of dialkyl quaternary compounds for improved softening when applied to synthetic blends. He also teaches in U.S. Pat. No. 4,134,840 that ether carboxylates can be added to improve softening of synthetic blends. The additions described above are pallative and do not address the basic problem intrinsic to the molecule.

DETAILED DESCRIPTION OF THE INVENTION

In accordance with this invention, quaternary ammonium compounds are provided represented by the general formula:

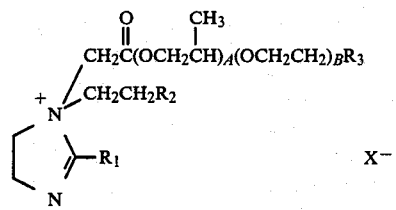

wherein $R_1$ is an n-alkyl, branched alkyl, alkenyl, branched alkenyl alkadienyl or branched alkadienyl group containing 8 to 21 carbon atoms; $R_2$ is a radical selected from the group consisting of (a) —OH, (b) amide radicals each of which has the structure

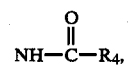

(c) a substituted imidazolinium group which has the structure:

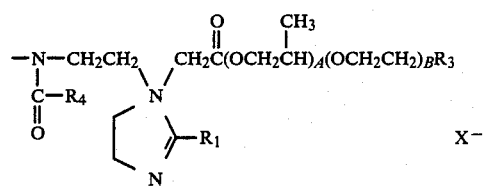

$R_3$ is a radical which has the structure

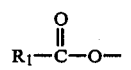

or —$OR_5$; $R_4$ is an alkyl or alkenyl group containing 1 to 17 carbon atoms; $R_5$ is $R_1$ or mono or dialkyl phenyl; A is an integer of from 0 to 20 and B is an integer of from 0 to 20 and $A+B>0$; x is either chlorine or bromine are provided.

The most preferred compounds are those wherein $R_1$ is $C_{17}H_{35}$—; $R_2$ is

or a substituted imidazolinium group which as the structure:

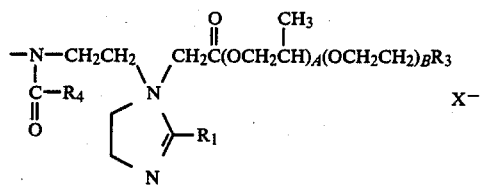

$R_3$ is $-O\overset{O}{\overset{\|}{C}}C_{17}H_{33}$; $R_4$ is $C_{17}H_{35}$; A is 0, 4 or 8;

B is 0, 4 or 8; x = Cl.

The compounds of this invention are prepared by one of two general methods. The first method involves the reaction of one mole of diethylenetriamine with one mole of a carboxylic acid containing 10 to 22 carbon atoms and one mole of a carboxylic acid containing 1 to 17 carbon atoms to form a diamidoamine which then cyclizes to from a 1-substituted imidazoline according to the following equation.

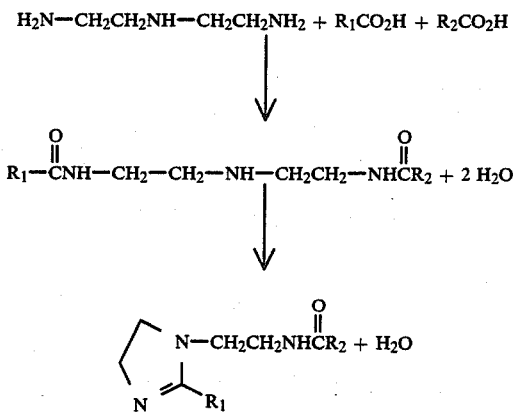

The imidazoline formed in the above reaction is then quaternized with one mole of an ester of chloroacetic acid that contains a polyalkyleneoxide group esterified with a carboxylic acid containing 10 to 22 carbon atoms or a polyalkoxylated mono or dialkyl phenol according to the following equation:

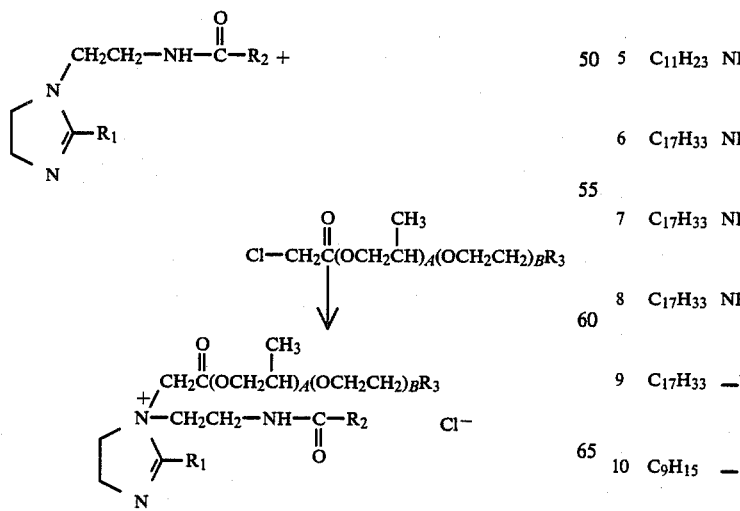

The following examples further serve to illustrate the synthesis of the compounds described in this invention, but are not intended to limit the invention. The compounds in Examples 1 through 11 are preared according to the following method and refer to the general formula:

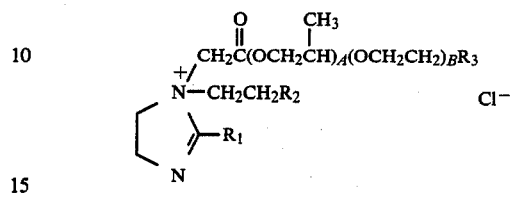

PREPARATION OF IMIDAZOLINE

Charge one mole of diethylene triamine, one mole of oleic acid, and one mole of heptanoic acid into a three neck glass reaction flask equipped with a stirrer, $N_2$ inlet, thermometer, and Dean Stark trap with Alihn condenser. Heat mixture with $N_2$ purge and agitation to 200° C. and maintain with continuous removal of water until the acid value falls below 5 (mg KOH/g) and the percent tertiary amine is greater than 65, (as measured by the tertiary amine/total amine values).

QUATERNIZATION

One mole of oleyl $-\Delta^2-$imidazoline and 1.0 to 1.2 moles of Polypropylene glycol 425 oleate chloroacetate are heated at 50°-60° C. in an open beaker until the total amine value falls below 3 (mg KOH/g).

| Ex | $R_1$ | $R_2$ | $R_3$ | A | B |
|---|---|---|---|---|---|
| 1 | $C_{17}H_{33}$ | $-NHCC_{17}H_{33}$ ‖ O | $OCC_{17}H_{33}$ ‖ O | 0 | 4 |
| 2 | $C_{17}H_{33}$ | $-NHCC_6H_{13}$ ‖ O | $-OCC_{17}H_{33}$ ‖ O | 0 | 4 |
| 3 | $C_{17}H_{33}$ | $-OH$ | $OCC_{17}H_{33}$ ‖ O | 7 | 0 |
| 4 | $C_{17}H_{33}$ | $NHCC_6H_{13}$ ‖ O | $OCC_{17}H_{33}$ ‖ O | 0 | 9 |
| 5 | $C_{11}H_{23}$ | $NHCC_3H_7$ ‖ O | $OCC_{17}H_{33}$ ‖ O | 0 | 4 |
| 6 | $C_{17}H_{33}$ | $NHCC_6H_{13}$ ‖ O | $OCC_{11}H_{23}$ ‖ O | 0 | 4 |
| 7 | $C_{17}H_{33}$ | $NHC_6H_{13}$ ‖ O | $OCC_{17}H_{35}$ ‖ O | 7 | 3 |
| 8 | $C_{17}H_{33}$ | $NHCC_6H_{13}$ ‖ O | $OCC_{17}H_{35}$ ‖ O | 7 | 1 |
| 9 | $C_{17}H_{33}$ | $-NCC_{17}H_{33}$ ‖ O | $-OCC_{17}H_3$ ‖ O | 0 | 16 |
| 10 | $C_9H_{15}$ | $-OCC_{17}H_{33}$ ‖ O | Sorbitan Monooleate | 0 | 20 |

-continued

| Ex | R₁ | R₂ | R₃ | A | B |
|---|---|---|---|---|---|
| 11 | $C_{17}H_{33}$ | $-OCC_{17}$<br>‖<br>O | [phenyl-O- with $C_9H_{19}$] | 0 | 4 |
| 12 | $C_{17}H_{33}$ | $-OH$ | $-OCC_{17}H_{35}$ | 0 | 7 |
| 13 | $C_{17}H_{33}$ | $NHCC_{17}H_{33}$ | [phenyl-O- with two $C_9H_{19}$] | 0 | 4 |

A second general method involves the reaction of one mole of tetraethylene pentamine and three moles of a carboxylic acid containing 10 to 22 carbon atoms to form a triamidodiamine which then cyclizes to form a bis-imidazolino-amide according to the following equation:

$$3R_1COH + NH_2CH_2CH_2NHCH_2CH_2NHCH_2CH_2NHCH_2CH_2NH_2$$

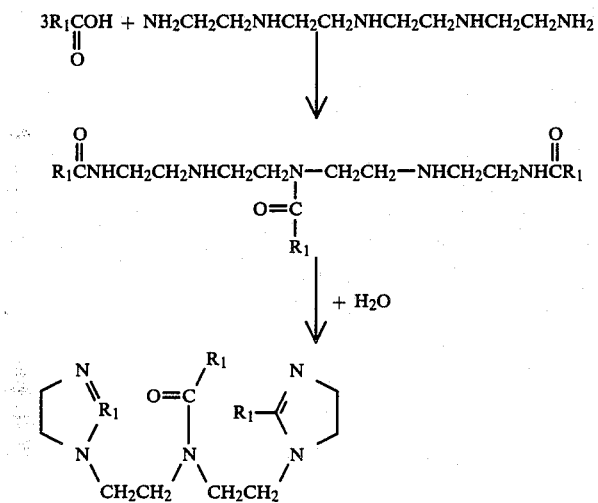

+ H₂O

The imidazoline formed in the above reaction is then quaternized with 2 moles of an ester of chloroacetic acid that contains a polyalkeneoxide group esterified with a carboxylic acid containing 10 to 22 carbon atoms according to the following equation:

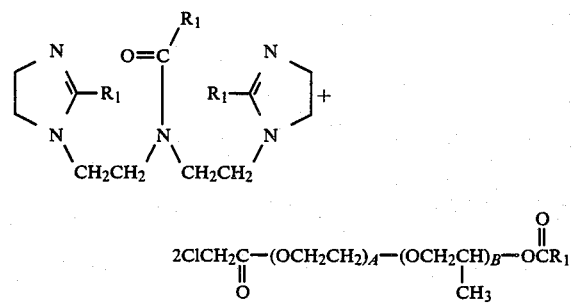

The compounds in Examples 12–14 are prepared according to the following method and refer to the general formula:

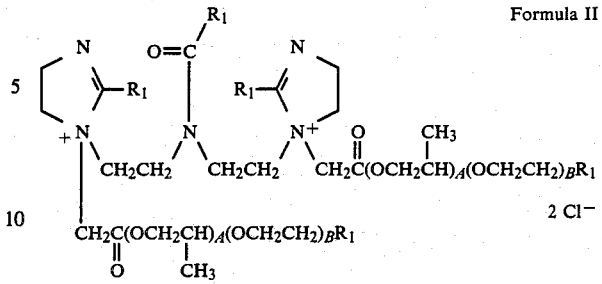

Formula II wherein R₁ is as defined above wherein A is an integer from 0 to 20 and B is an integer from 0 to 20 and A+B>0.

PREPARATION OF DI-IMIDAZOLINE

Charge one mole of tetraethylene pentamine and 3 moles of oleic acid into a three neck glass reaction flask equipped with a stirrer, N₂ inlet, thermometer, and Dean Stark trap with Alihn condenser. Heat mixture with N₂ purge and agitation to 200° C. and maintain with continuous removal of water until the acid value falls below 5 (mg KOH/g) and the percent tertiary amine is greater than 65, (as measured by the tertiary amine/total amine values).

QUATERNIZATION

One mole of di-imidazoline and 2.0 moles of Polyethylene glycol 400 stearate chloroacetate are heated at 50°–60° C. in an open beaker until the total amine value falls below 3 (mg KOH/g).

The following examples further serve to illustrate the synthesis of the compounds described in this invention.

| Ex. Formula II | R₁ | A | B |
|---|---|---|---|
| 14 | $C_{17}H_{33}-$ | 0 | 8 |
| 15 | $C_{17}H_{33}-$ | 8 | 0 |
| 16 | $C_{17}H_{33}-$ | 4 | 4 |
| 17 | $C_{17}H_{35}-$ | 4 | 4 |
| 18 | $C_{17}H_{35}-$ | 0 | 8 |
| 19 | $C_{17}H_{35}-$ | 8 | 0 |
| 20 | Cocobetainyl | 0 | 8 |

Compounds of this invention were compared to standard compounds commercially available using AATCC Test Method 117-1979. The color fastness heat test uses a 400 F hot iron which is applied for 60 and 180 seconds. The color is rated on a 1–5 basis for yellowness, (5 being the most yellow).

| Compound | CAS Number | Yellowness |
|---|---|---|
| Class #1 Compound | 68122-86-1 | 4 |
| Class #2 Compound | 61789-81-9 | 4 |
| Class #3 Compound | 65098-88-6 | 5 |
| Class #4 Compound | 68308-45-2 | 4 |
| Compounds of Formula II - wherein $R_1 = C_{17}H_{35}$, A = 0, B = 8 (Developmental Quat #1) | | 1 |
| Compounds of Formula II - wherein $R_1 = C_{17}H_{33}$, A = 0, B = 8 (Developmental Quat #2) | | 2 |

The compatibility of these novel compounds with tissue was tested. In these tests a 0.1 ml sample of the material being tested was introduced into one eye of an albino rabbit, the other eye serves as a control. Observations were made after 1 day, 2 days, 3 days, 4 days and 7 days. Second and third instillations were made after 24 and 48 hours. Results can vary from substantially no change to complete corneal opacity. Ocular lesions are scored for the cornea, iris and conjuctiva on a scale of 1 to 6 with the higher score indicating graded ocular irritation. The scores are added to the six rabbits tested and an average is obtained. Typical results for the standard quaternary compound used in hair conditioning (stearyldimethylbenzyl ammonium chloride) and a representative of the new compounds being tested are as follows:

| Ocular Irritation | | | | | |
|---|---|---|---|---|---|
| 1 | 2 | 3 | 4 | 7 | |
| | | Days | | | Dermal Irritation |
| Developmental Compound #1 | | | | | |
| 2 | 0 | 0 | 0 | 0 | 0.83 |
| Comparison Product | | | | | |
| Stearyldimethylbenzyl ammonium chloride | | | | | |
| 34 | 29 | 27 | 26 | 26 | 3.75 |

The data shows dramatically that the novel quaternary compounds are very mild, while the standard quaternary compounds used in hair conditioning are severe irritants.

WET COMB OUT TEST

A laboratory test was conducted to screen the wet comb properties of a representative member of the family of novel compounds. Hair swatches are purchased from a supply of human hair from the said head. Each test swatch contains 7 grams of hair, 11 inches in length. The hair is tied tightly 1 inch from one end with string. The swatch is pre-cleaned with a 3% solution of Ammonium Lauryl Sulfate. Subsequently the swatch is washed under running tap water. The hair is then squeezed out and while still damp dipped into a 200 ml solution of 0.2% active Quat. Another rinse is made, then the swatch is blotted dry. Holding the hair swatch comb the hair is rapidly as possible, alternating the side of the swatch combed. The time needed to get one smooth free stroke without tangling is recorded. Typical results for the standard quaternary compound used in hair conditioning (stearyldimethylbenzyl ammonium chloride) range from 12-14 seconds.

| Rinse Conditioner (Wet Comb Test) | |
|---|---|
| Product | Time in Seconds |
| Developmental Compound #1 | 10 |
| Developmental Compound #2 | 13 |
| Stearyldimethyl benzyl ammonium chloride | 12 |

As can be seen, this compound gives significant conditioning properties to hair, and coupled with their mild nature with regard to skin and eyes, making it a prime candidate for cosmetic applications.

The compounds of this invention, or mixtures thereof can be formulated into softeners or conditioners that are applied directly in aqueous solution by themselves or formulated with known anionics and builders to prepare finished conditioner/detergent systems.

The compounds of this invention also were used in the treatment of bleached-pine kraft pulp in the form of an aqueous slurry with a pulp consistency of 0.5%. Handsheets were formed from the pulp on a laboratory handsheet machine to produce 20 centimeters ×20 centimeters pulp sheets with basis weights of 400 g/m$^2$ (245 pounds per 3,000 ft$^2$ ream). After the sheets were formed, pressed, and dried by the standard procedure, the debonding effect was evaluated by determining the fiber-to-fiber internal bond strength of these sheets by means of a Olin tester (BF Perkins Company) as described in TAPPI method T 403 os-76. The water absorption rate of the pulp was measured according to the Klemm procedure as described in SCAN P13:64 and by the fiber absorbent quality method SCAN C33:80. The debonding effect was expressed as a percent mullen reduction which is calculated as follows:

$$\% \text{ Mullen Reduction} = \frac{\text{Burst strength untreated} - \text{Burst strength treated}}{\text{Burst strength untreated}} \times 100\%$$

The untreated pulp would have a percent mullen reduction of 0 while debonded pulp would have values greater than 0 so that the greater the degree of debonding, the greater the percent mullen reduction. The water absorbency properties of treated pulp are measured by the FAQ test (SCAN C33:80 method). In this method, approximately 4.0 grams of pulp are defiberized for 20 seconds in a Waring Blender and then conditioned for 24 hours at 25° C. and 50% relative humidity. The fluffed pulp sample is then placed in the FAQ apparatus and the rate of water absorption is measured under a load of 2.5 kPa. The fluff pulp sample is then allowed to be saturated completely and the water absorption capacity is determined by substracting the weight of the saturated test sample from the original dry weight of the fiber. The absorption time per 4 grams of sample is the average of 5 determinations. The relative absorbency is the water absorption time of the treated pulp sample divided by the water absorption time for the untreated pulp sample.

By these methods, it was determined that the general fiber softening properties of the compounds of the invention or mixtures thereof extend to use in debonding cellulose pulp.

The following examples, while not limiting the invention thereto will serve to illustrate the instant invention.

EXAMPLES

EXAMPLE #21

An aqueous solution containing 0.1 to 1.0% novel developmental compound #1 is applied to a cotton polyester blend by exhaustion or using conventional dip and nip technology. The material acts as a lubricant for the processing of the fiber and a non-yellowing softener.

EXAMPLE #22

A solution of 1-5% active novel developmental compound #1 is applied to the hair in a creme rinse. Perfume and color can be added to this simple cost effective conditioner.

EXAMPLE #23

A solution is prepared of one part developmental compound #1 and one part stearyl alcohol. The active level is cut to 3-10% by weight with water. This solution is applied to the hair in a creme rinse.

EXAMPLE #24

A solution of 0.25-1.50% developmental compound #2 is applied to a polyester blend by exhaustion or using conventional dip and nip technology. The material acts as lubricant for the processing of the fiber and a non-yellowing softener.

EXAMPLE #25

A conditioning shampoo formulation can be prepared using the following general formulation:

| Material (by weight) | CAS Number | Percent |
|---|---|---|
| Water | | 38.6 |
| Amphoteric 18* | 68650-39-5 | 40.0 |
| Amphoteric 12* | 68630-96-6 | 11.4 |
| Novel Quaternary #1 | | 10.0 |
| | | 100.0 |

*CTFA Names and CAS numbers.

Excellent wet comb and conditioning effects are noted with the above formulation.

EXAMPLE #26

A solution of 1-5% active novel quaternary compound #1 is applied to the rinse cycle of in a laundry application. The product gives excellent softness, hand and soil release properties.

EXAMPLE #27

A solution of 5% developmental compound #1 is formulated with a standard phosphate laundry formulation:

| | |
|---|---|
| Neodol 25-7 | 15.0 |
| Sodium Tri Poly Phosphate | 40.0 |
| Sodium Metasilicate Pentahydrate | 5.0 |
| Carboxy Methyl Cellulose | 0.5 |
| Sodium Sulfate | 29.5 |
| Sodium Carbonate | 5.0 |
| Compound #1 | 5.0 |

EXAMPLE #28

A solution of 2% developmental compound #2 is formulated with a standard phosphate free laundry formulation:

| | |
|---|---|
| Neodol 25-7 | 10.0 |
| Sodium Carbonate | 25.0 |
| Sodium Meta Silicate Pentahydrate | 7.0 |
| Sodium Sesquicarbonate | 10.0 |
| Sodium Sulfate | 42.0 |
| Carboxy Methyl Cellulose | 1.0 |
| Compound #2 | 2.0 |

EXAMPLE #29

A solution of 3% of the compound of Example 17 is formulated with a standard hand wash formulation:

| | |
|---|---|
| Neodol 25-7 | 10.0 |
| Lauric Diethanolamide | 5.0 |
| Cocobetaine | 10.0 |
| Water | Q.S. |
| Compound #1 | 3.0 |

EXAMPLE #30

A solution of 4% of the compound of Example 20 is formulated with a standard anti-static laundry formulation:

| | |
|---|---|
| Nonyl Phenol - 9 | 20.0 |
| Palmitic Betaine | 10.0 |
| DoDecyl Benzene Sulfonic Acid | 10.0 |
| DEA | 10.0 |
| Compound #1 | 4.0 |
| Cocamide DEA | 5.0 |
| Water | Q.S. |

GENERAL TREATMENT PROCEDURE

To a pulp slurry containing 17 grams of bleached sulfate pulp and 2,000 milliliters of water are added 4 milliliters of 1% solution of the debonder. The pH of the slurry is adjusted to 6-6.5. Sheets were then formed in a laboratory sheet machine in the usual manner. After drying, the sheets were examined with respect to burst strength and adsorption time as discussed above.

This example compares the burst strength and absorbency of pulps treated with various debonding compositions containing various quaternary ammonium compounds and nonionic surfactants.

The following data shows the performance of debonder formulations of this invention:

| Additive | Debonding Efficiency % Mullen Reduction | Relative Water Absorbency FAQ Absorbency |
|---|---|---|
| None | 0 | 1.00 |
| A | 47 | 0.78 |
| B | 57 | 0.89 |
| C | 53 | 0.82 |
| D | 52 | 0.85 |
| E | 51 | 0.80 |

A  31.2% Compound of Example 6,
    34.4% polyethylene glycol 200 monooleate
    34.4% polyethylene-propylene glycol monooleate
B  31.2% Compound of Example 12,
    22.9% polyethylene glycol 200 monooleate
    45.9% polyethylene-propylene glycol monooleate
*Reference Example
C  31.2% Compound of Example 4,
    22.9% polyethylene glycol 200 monooleate
    45.9% polyethylene-propylene glycol monooleate
D  39.6% Compound of Example 3,
    50.5% polyethylene glycol 425 monooleate
    0.9% propylene glycol
E  39.6% Compound of Example 13,
    59.4% polypropylene glycol 425 monooleate
    1.0% propylene glycol
*Reference Example

We claim:
1. A compound of the formula:

Formula I

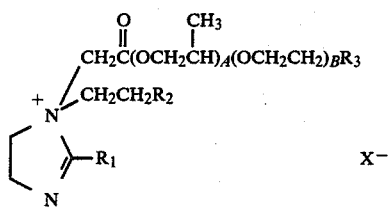

wherein $R_1$ is an n-alkyl, branched alkyl, alkenyl, branched alkenyl alkadienyl or branched alkadienyl group containing 8 to 21 carbon atoms; $R_2$ is a radical selected from the group consisting of (a) —OH, (b) amide radicals each of which has the structure

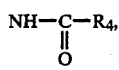

(c) a substituted imidazolinium group which has the structure:

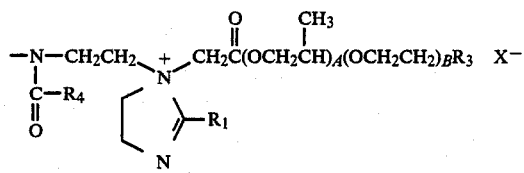

$R_3$ is a radical which has the structure

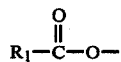

or $OR_5$; $R_4$ is an alkyl or alkenyl group containing 1 to 15 carbons atoms; $R_5$ is $R_1$ or monononyl phenyl or dinonyllphenyl; A is an integer of from 0 to 20 and B is an integer of from 0 to 20 and $A+B>0$; x is either chlorine or bromine.

2. A compound of claim 1, wherein $R_1$ is $C_{17}H_{35}$—; $R_2$ is

or a substituted imidazolinium group which has the structure:

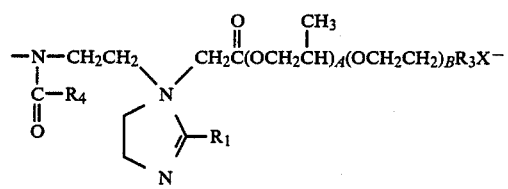

$R_3$ is

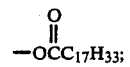

$R_4$ is $C_{17}H_{35}$; A is 0, 4 or 8; B is 0, 4 or 8; x=Cl.

3. A method for softening and conditioning fibers, hair or skin comprising applying to said fibers, hair or skin an effective amount of an aqueous composition comprising a compound of claim 1, or mixtures of said compounds.

4. A method as in claim 3, which comprises a cellulose pulp debonding method.

5. A method as in claim 3, wherein said composition further comprises a laundry formulation.

6. A method as in claim 3, wherein said composition comprises 1–5% of the compound of Formula I.

7. A method as in claim 3, wherein said composition further comprises cosmetic or personal care formulations.

8. A method as in claim 7, wherein said composition further comprises shampoo or creme rinse formulations.

* * * * *